(12) United States Patent
Ogura et al.

(10) Patent No.: US 6,475,155 B2
(45) Date of Patent: Nov. 5, 2002

(54) PULSE-WAVE-PROPAGATION-RELATING INFORMATION OBTAINING APPARATUS AND ARTERIAL-BIFURCATE-PORTION DETERMINING APPARATUS

(75) Inventors: Toshihiko Ogura; Chikao Harada; Takashi Honda; Kiyoyuki Narimatsu, all of Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/726,452

(22) Filed: Dec. 1, 2000

(65) Prior Publication Data

US 2001/0003792 A1 Jun. 14, 2001

(30) Foreign Application Priority Data

Dec. 8, 1999 (JP) ............................................. 11-348370

(51) Int. Cl.[7] ................................................ A61B 5/00
(52) U.S. Cl. ....................................... 600/500; 600/587
(58) Field of Search ............................... 600/485, 500.3, 600/587

(56) References Cited

U.S. PATENT DOCUMENTS

| | | | | |
|---|---|---|---|---|
| 5,649,543 A | * | 7/1997 | Hosaka et al. | 600/500 |
| 5,704,363 A | | 1/1998 | Amano | |
| 5,755,669 A | * | 5/1998 | Ono et al. | 600/500 |
| 5,876,346 A | * | 3/1999 | Corso | 600/485 |
| 5,876,348 A | * | 3/1999 | Sugo et al. | 600/500 |
| 6,186,954 B1 | * | 2/2001 | Narimatsu | 600/500 |
| 6,315,734 B1 | * | 11/2001 | Nunome | 600/500 |

FOREIGN PATENT DOCUMENTS

JP  10-309272  11/1998

* cited by examiner

*Primary Examiner*—Robert L. Nasser
(74) *Attorney, Agent, or Firm*—Oliff & Berridge, PLC

(57) ABSTRACT

An apparatus for obtaining a pulse-wave-propagation-relating information of a living subject, including a bifurcate-portion determining device which determines a bifurcate portion of an artery of the subject that is present under a skin of the subject, a pulse-wave-detect-portion determining device for determining, based on the determined bifurcate portion of the artery, a pulse-wave-detect portion of the artery from which a pulse wave is detected, a reference-point determining device for determining a reference point on the pulse wave detected from the determined pulse-wave-detect portion of the artery, and a pulse-wave-propagation-relating-information obtaining device for obtaining the pulse-wave-propagation-relating information of the subject based on the determined reference point of the pulse wave.

13 Claims, 7 Drawing Sheets

PULSE-WAVE-PROPAGATION-RELATING INFORMATION OBTAINING APPARATUS AND ARTERIAL-BIFURCATE-PORTION DETERMINING APPARATUS

BACKGROUND OF THE INVENTION

1. Field of the Invention

The present invention relates to an apparatus for determining a bifurcate portion of an artery which is present under skin of a living subject, and an apparatus for detecting a pulse wave from a pulse-wave-detect portion of the artery that is determined based on the bifurcate portion and obtaining accurate pulse-wave-propagation-relating information based on the pulse wave.

2. Discussion of Related Art

As physical information relating to circulatory organ of a living subject, there is known a pulse-wave propagation time in which a pulse wave propagates between two predetermined portions of an artery, and a pulse-wave propagation velocity which is calculated based on the pulse-wave propagation time and the distance between the two predetermined portions of the artery. Hereinafter, the pulse-wave propagation time and the pulse-wave propagation velocity will be referred to as the pulse-wave-propagation-relating information or PWP-relating information. The PWP-relating information reflects the blood pressure (BP) of the subject. Therefore, it has been practiced to monitor the PWP-relating information and, when a change thereof is detected, start an automatic BP measurement on the subject. It is also practiced to obtain, each time the heart of the subject beats, a piece of PWP-relating information and estimate, based on the obtained information, a BP value of the subject. In addition, since the PWP-relating information reflects the flexibility of arteries of the subject, the information is utilized to measure the degree of arteriosclerosis, and/or the degree of peripheral resistance, of the subject.

Meanwhile, a pulse-wave propagation time is obtained by detecting respective heartbeat-synchronous signals from two portions of an artery of a living subject and subtracting a first time at which a first heartbeat-synchronous signal from a first portion of the artery from a second time at which a second heartbeat-synchronous signal from a second portion of the artery; and a pulse-wave propagation velocity is obtained by dividing the distance between the first and second portions of the artery by the pulse-wave propagation time. Two sensors are used to detect the first and second heartbeat-synchronous signals from the first and second portions of the artery, respectively. At least one of the two sensors is provided by a pressure-pulse-wave sensor which presses an appropriate portion of the artery via skin of the subject and detects, from the pressed portion, a pressure pulse wave which is produced in synchronism with the heartbeat of the subject. In this case, usually, a characteristic point of the waveform of the thus detected pressure pulse wave, such as a rising point (i.e., a minimum-value point), a maximum-slope point, a maximum-value point, or a well-known "notch" point, is employed as a reference point to obtain a piece of PWB-relating information.

However, it is difficult for a living subject or a medical staff (e.g., a doctor or a nurse) to iteratively press the pressure-pulse-wave sensor against substantially the same portion of the artery to detect a pressure pulse wave in respective measurements at different times. Therefore, the distance between the two portions of the artery that is used to measure the pulse-wave propagation time or velocity may change between the different measurements. Accordingly, the thus measured propagation times or velocities cannot enjoy a satisfactory accuracy. Thus, it is difficult to compare the propagation times or velocities measured at different times, with each other, or detect a time-wise change of the propagation times or velocities.

In this background, one may possibly think to use a bone near an artery, as a reference point, and press the pressure-pulse-wave sensor at a measure point distant by a predetermined distance from the reference point. For example, a base portion of a costa of each living subject may be used as a reference point, and a predetermined distance from the reference point to a measure point above a carotid artery may be recorded or stored for the each subject. In this case, in each of respective measurements at different times, the sensor is pressed at the measure point above the carotid artery that is distant by the predetermined distance from the reference point. However, generally, a living person is mechanically soft and it is difficult to fix his or her joints. Thus, it is difficult to fix his or her head or neck in the same posture in each measurement. Therefore, even if the sensor may be accurately pressed at the measure point above the carotid artery distant by the predetermined distance from the base portion of the costa, the sensor may not be accurately pressed against substantially the same portion of the artery in every measurement.

SUMMARY OF THE INVENTION

It is therefore an object of the present invention to provide a pulse-wave-propagation-relating-information obtaining apparatus and an arterial-bifurcate-portion determining apparatus each of which assures accurate measurement of pulse-wave-propagation-relating information.

To achieve the above object, the present inventors have carried out an extensive study, and found the fact that when a bifurcate portion of an artery, or a portion of the artery distant by a predetermined distance from the bifurcate portion is used as a pulse-wave-detect portion, accurate pulse waves can be detected because those pulse waves are free of the conventionally encountered problem that subject's head or neck cannot be fixed to the same posture in every measurement because of his or her mechanical softness and/of the difficulty of fixing of his or her joints. The present invention has been developed based on this finding.

The present invention provides a pulse-wave-propagation (PWP) relating information obtaining apparatus and an arterial-bifurcate-portion determining apparatus which have one or more of the following technical features that are described below in respective paragraphs given parenthesized sequential numbers (1) to (8). Any technical feature that includes another technical feature shall do so by referring, at the beginning, to the parenthesized sequential number given to the latter feature. However, the following technical features and the appropriate combinations thereof are just examples to which the present invention is by no means limited.

(1) According to a first feature of the present invention, there is provided an apparatus for obtaining a pulse-wave-propagation-relating information of a living subject, comprising a bifurcate-portion determining device which determines a bifurcate portion of an artery of the subject that is present under a skin of the subject; a pulse-wave-detect-portion determining means for determining, based on the determined bifurcate portion of the artery, a pulse-wave-detect portion of the artery from which a pulse wave is detected; a reference-point determining means for determining a reference point on the pulse wave detected from the determined pulse-wave-detect portion of the artery; and a pulse-wave-propagation-relating-information obtaining means for obtaining the pulse-wave-propagation-relating information of the subject based on the determined reference point of the pulse wave.

In the present PWP-relating-information obtaining apparatus, the pulse-wave-detect-portion determining means determines, based on the bifurcate portion of the artery determined by the bifurcate-portion determining device, a pulse-wave-detect portion of the artery, and the reference-point determining means determines a reference point on the pulse wave detected from the determined pulse-wave-detect portion of the artery. Then, the PWP-relating-information obtaining means obtains the PWP-relating information of the subject based on the determined reference point of the pulse wave. Thus, the pulse-wave-detect portion is determined based on the bifurcate portion of the artery itself, and the PWP-relating information is obtained based on the reference point of the pulse wave detected from the pulse-wave-detect portion. The thus determined pulse-wave-detect portion of the artery is not changed by the change of posture of the living subject. Therefore, accurate PWP-relating information can be obtained. This advantage is amplified under such measurement conditions that a distance between the pulse-wave-detect portion and another portion of the artery is short, i.e., a time in which the pulse wave propagates between the two portions of the artery is short, for example, in such a case where PWB-relating information is obtained from between the reference point of the pulse wave detected from a carotid artery and a reference point on the waveform of a photocardiogram or an electrocardiogram.

(2) According to a second feature of the present invention that includes the first feature (1), the bifurcate-portion determining device comprises a pressure-pulse-wave sensor including a plurality of pressure-sensing elements which are arranged at a first regular interval of distance in an arrangement direction over a distance longer than a diameter of the artery, and each of which produces a pulse-wave signal representing a pressure pulse wave propagated thereto from the artery; a distribution-curve obtaining means for obtaining a plurality of distribution curves each of which represents a relationship between respective positions of the pressure-sensing elements in the arrangement direction and respective amplitudes or respective minimum magnitudes of the respective pressure pulse waves represented by the respective pulse-wave signals produced by the pressure-sensing elements which are located at a corresponding one of a plurality of curve-obtain positions which are arranged at a second regular interval of distance in a predetermined range in a lengthwise direction of the artery and at each of which the pressure-sensing elements arranged in the arrangement direction traverse the artery; and a bifurcate-portion determining means for determining, based on the distribution curves respectively corresponding to the curve-obtain positions, the bifurcate portion of the artery in the predetermined range in the lengthwise direction of the artery. In the present PWP-relating information obtaining apparatus, the distribution-curve obtaining means obtains a plurality of distribution curves each of which represents a relationship between respective positions of the pressure-sensing elements in the arrangement direction and respective amplitudes or respective minimum magnitudes of the respective pressure pulse waves represented by the respective pulse-wave signals produced by the pressure-sensing elements which are located at a corresponding one of a plurality of curve-obtain positions which are arranged at a second regular interval of distance in a predetermined range in a lengthwise direction of the artery and at each of which the pressure-sensing elements arranged in the arrangement direction traverse the artery; and the bifurcate-portion determining means determines, based on the distribution curves respectively corresponding to the curve-obtain positions, the bifurcate portion of the artery. Thus, an accurate bifurcate-portion can be determined, and accordingly an accurate pulse-wave-detect portion can be determined, so that accurate PWP-relating information can be obtained.

(3) According to a third feature of the present invention that includes the second feature (2), the bifurcate-portion determining means determines the bifurcate portion of the artery based on at least one second interval between the two curve-obtain positions one of which corresponds to the distribution curve having a single peak and the other of which corresponds to the distribution curve having two peaks. In the present PWP-relating information obtaining apparatus, the bifurcate-portion determining means determines the bifurcate portion based on one or more intervals between two curve-obtain positions one of which corresponds to a distribution curve having a single peak and the other of which corresponds to another distribution curve having two peaks, more preferably, within the interval or intervals. Therefore, an accurate bifurcate portion can be determined, and accordingly accurate PWP-relating information can be obtained.

(4) According to a fourth feature of the present invention that includes any one of the first to third features (1) to (3), the pulse-wave-detect-portion determining means determines, as the pulse-wave-detect portion of the artery, a portion of the artery that is distant, by a predetermined distance, downstream of the determined bifurcate portion of the artery in a direction in which blood flows in the artery. In the present PWP-relating information obtaining apparatus, a portion of the artery that is not adversely influenced by turbulent flows produced in the vicinity of the bifurcate portion can be determined as the pulse-wave-detect portion of the artery, and an a good pulse wave having an accurate waveform can be detected from the pulse-wave-detect portion of the artery. Thus, an accurate reference point can be determined on the waveform of pressure pulse wave. In addition, since a distance by, or a time in, which the pressure pulse wave propagates is increased, the accuracy with which pulse-wave-propagation velocity is calculated based on time difference is increased.

(5) According to a fifth feature of the present invention that includes any one of the thirst to fourth features (1) to (4), the pulse-wave-propagation-relating-information obtaining means obtains the pulse-wave-propagation-relating information of the subject based on a time difference between a reference point on a waveform of an electrocardiogram or a phonocardiogram and the determined reference point of a pressure pulse wave as the pulse wave detected from the determined pulse-wave-detect portion of a carotid artery as the artery. In the present PWP-relating information obtaining apparatus, a pressure pulse wave having substantially the same waveform as that of an aortic pressure pulse wave can be detected from the carotid artery, and a time difference can be measured based on a reference point determined on the accurate waveform of the pressure pulse wave detected from the pulse-wave-detect portion of the carotid artery. Therefore, though the carotid artery is not so distant from the heart of the subject, accurate PBP-relating information of the subject can be obtained.

(6) According to a sixth feature of the present invention that includes the second feature (2), the pressure-pulse-wave sensor includes the pressure-sensing elements which are arranged in a matrix such that the elements are arranged at a regular interval of distance along a plurality of first straight lines parallel to each other and at a regular interval of distance along a plurality of second straight lines which are parallel to each other and are perpendicular to the first straight lines. The present PWP-relating-information obtaining apparatus need not employ a drive device for moving the pressure-pulse-wave sensor in the directions along the artery, in contrast to the case where the pressure pulse wave sensor includes only a single array of pressure-sensing elements which is adapted to intersect the artery when the sensor is applied to the subject.

(7) According to a seventh feature of the present invention, there is provided an apparatus for determining a bifurcate portion of an artery of a living subject that is present under a skin of the subject, comprising a pressure-pulse-wave sensor including a plurality of pressure-sensing elements which are arranged at a first regular interval of distance in an arrangement direction over a distance longer than a diameter of the artery, and each of which produces a pulse-wave signal representing a pressure pulse wave propagated thereto from the artery; a distribution-curve obtaining means for obtaining a plurality of distribution curves each of which represents a relationship between respective positions of the pressure-sensing elements in the arrangement direction and respective amplitudes or respective minimum magnitudes of the respective pressure pulse waves represented by the respective pulse-wave signals produced by the pressure-sensing elements which are located at a corresponding one of a plurality of curve-obtain positions which are arranged at a second regular interval of distance in a predetermined range in a lengthwise direction of the artery and at each of which the pressure-sensing elements arranged in the arrangement direction traverse the artery; and a bifurcate-portion determining means for determining, based on the distribution curves respectively corresponding to the curve-obtain positions, the bifurcate portion of the artery in the predetermined range in the lengthwise direction of the artery.

In the present bifurcate-portion determining apparatus, the distribution-curve obtaining means obtains a plurality of distribution curves each of which represents a relationship between respective positions of the pressure-sensing elements in the arrangement direction and respective amplitudes or respective minimum magnitudes of the respective pressure pulse waves represented by the respective pulse-wave signals produced by the pressure-sensing elements which are located at a corresponding one of a plurality of curve-obtain positions which are arranged at a second regular interval of distance in a predetermined range in a lengthwise direction of the artery and at each of which the pressure-sensing elements arranged in the arrangement direction traverse the artery, and the bifurcate-portion determining means determines, based on the distribution curves respectively corresponding to the curve-obtain positions, the bifurcate portion of the artery in the predetermined range in the lengthwise direction of the artery. Therefore, the present apparatus can accurately determine the bifurcate portion of the artery. In addition, since a pulse-wave-detect portion of the artery can be accurately determined based on the accurately determined bifurcate portion, accurate PWP-relating information can be obtained based on a pulse wave detected from the accurately determined pulse-wave-detect portion.

(8) According to an eighth feature of the present invention that includes the seventh feature (7), the bifurcate-portion determining means determines the bifurcate portion of the artery based on at least one second interval between the two curve-obtain positions one of which corresponds to the distribution curve having a single peak and the other of which corresponds to the distribution curve having two peaks. In the present bifurcate-portion determining apparatus, the bifurcate-portion determining means determines the bifurcate portion based on one or more intervals between two curve-obtain positions one of which corresponds to a distribution curve having a single peak and the other of which corresponds to another distribution curve having two peaks, more preferably, within the interval or intervals. Therefore, an accurate bifurcate portion can be determined, and accordingly an accurate pulse-wave-detect portion of the artery can be determined based on the bifurcate portion. Consequently accurate PWP-relating information can be obtained.

BRIEF DESCRIPTION OF THE DRAWINGS

The above and other objects, features, advantages and technical and industrial significance of the present invention will be better understood by reading the following detailed description of preferred embodiments of the invention, when considered in connection with the accompanying drawings, in which.

DETAILED DESCRIPTION OF PREFERRED EMBODIMENTS

Hereinafter, there will be described one embodiment of the present invention, by reference to the accompanying drawings.

Figure 1:
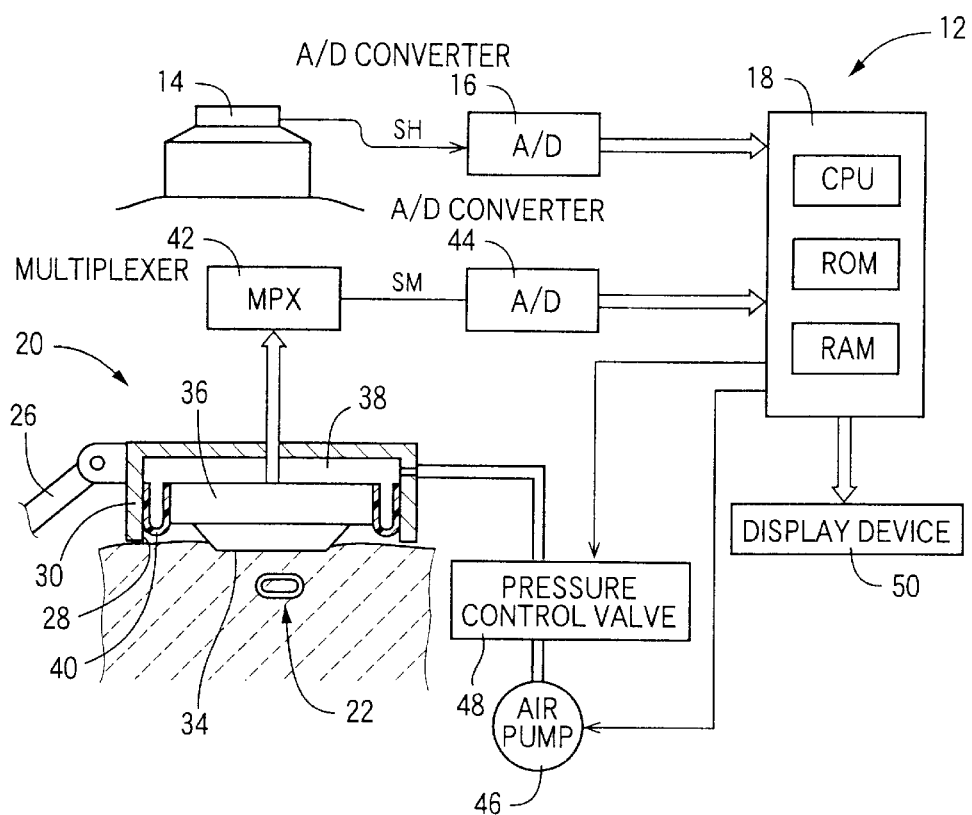
FIG. 1 is a diagrammatic view of the construction of a pulse-wave-propagation (PWP) relating information obtaining apparatus to which the present invention is applied.

FIG. 1 is a diagrammatic view for explaining a construction of a pulse-wave-propagation (PWP) relating information obtaining apparatus 12 to which the present invention is applied. The PWP-relating-information obtaining apparatus 12 includes an arterial-bifurcate-portion determining device to which the present invention is also applied. In FIG. 1, a heart-sound microphone 14 is one which is disclosed in Japanese Patent Document No. 10-309272. The microphone 14 is placed or worn on the chest of a living subject, to detect hear sounds produced from the heart of the subject, and outputs a phonocardiogram signal, SH, representing a phonocardiogram including the detected heart sounds. The signal SH is supplied to a control device 18 via an analog-to-digital (A/D) converter 16. The heart sounds of the phonocardiogram represented by the signal SH are heartbeat-synchronous pulses which are produced in synchronism with the heartbeat of the subject. Thus, in the present embodiment, the heart-sound microphone 14 functions as a heartbeat-synchronous-pulse sensor.

Figure 2:
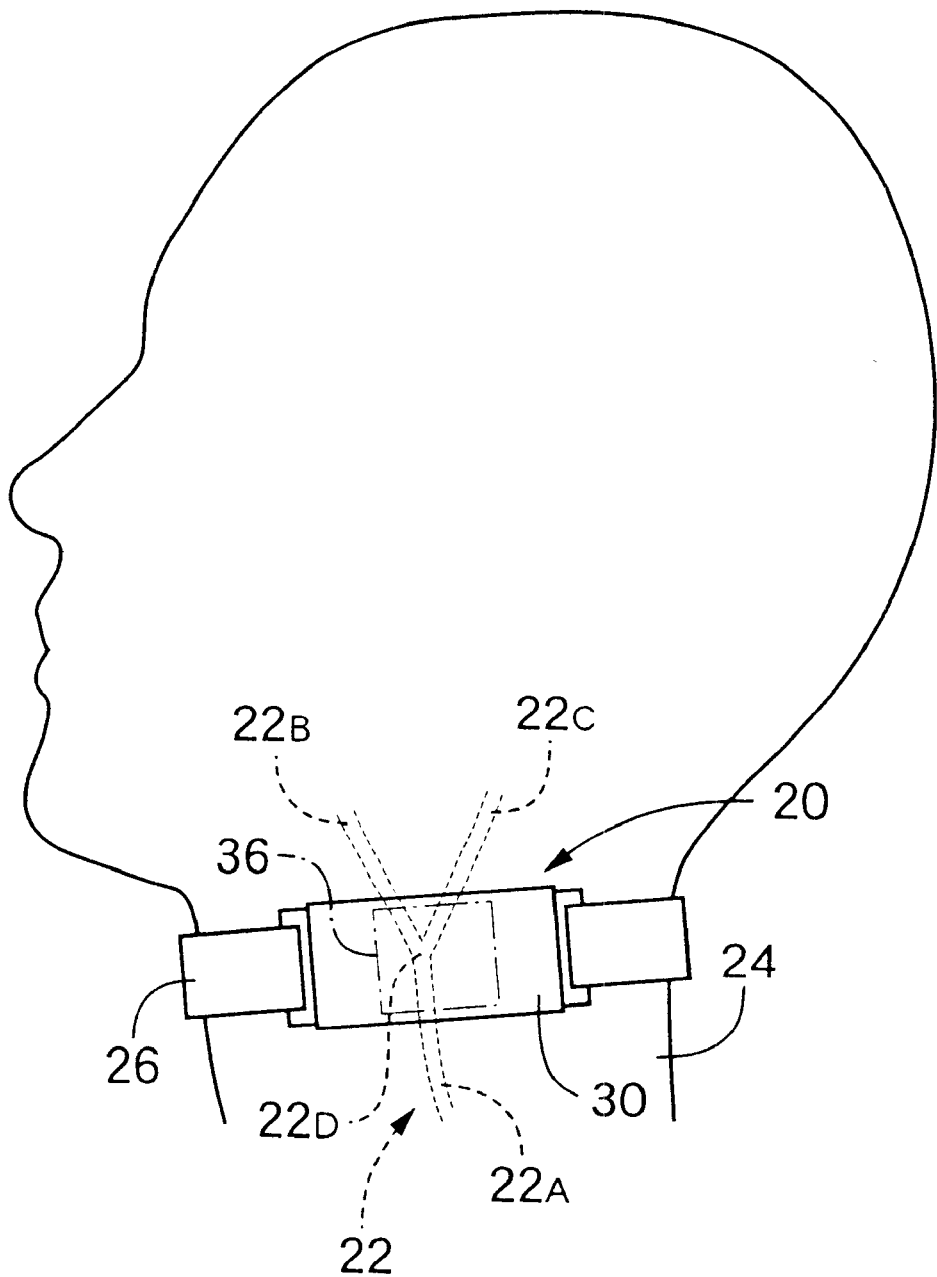
FIG. 2 is a view showing a state in which a pulse-wave detecting device of the apparatus of FIG. 1 is worn on a neck of a living subject.

A carotid-pulse-wave detecting device 20 includes a pressure-pulse-wave sensor 36 which detects a carotid pulse wave representing the change of blood pressure in a carotid artery 22 of the subject. As illustrated in detail in FIG. 2, the detecting device 20 is worn around a neck 24 of the subject with the help of a band 26, such that the sensor 36 is right above the carotid artery 22 via the skin of the subject. The carotid artery 22 includes a common carotid artery $22_A$, and an internal and an external carotid artery $22_B$, $22_C$ which are bifurcated from the common carotid artery 22A at a bifurcate portion $22_D$. The detecting device 20 is worn on the neck 24 such that a press surface 34 of the sensor 36 is pressed against the bifurcate portion $24_D$ of the carotid artery 22 via the skin.

Figure 3:
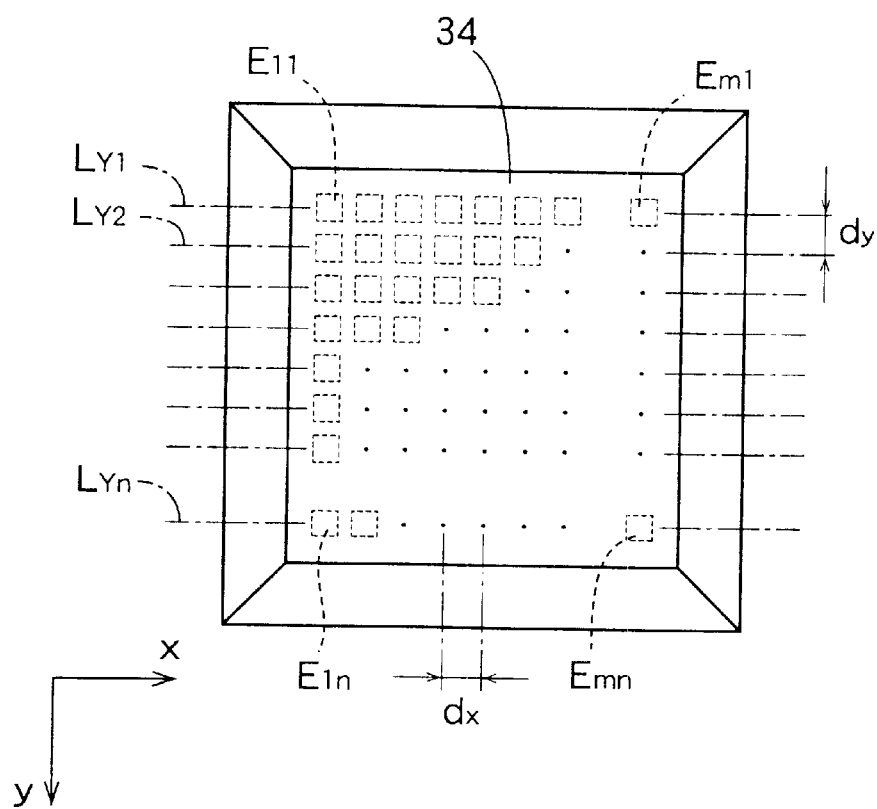
FIG. 3 is a view of a press surface of a pressure-pulse-wave sensor of the pulse-wave detecting device in which surface a plurality of pressure-sensing elements are arranged in an matrix.

The carotid-pulse-wave detecting device 20 includes a housing 30; the pressure-pulse-wave sensor 36; and an elastic diaphragm 40. The housing 30 has a container-like, rectangular-parallelepiped shape having an opening 28, and is worn on the neck 24 with the band 26 in such a manner that the opening 28 faces the body surface or skin of the subject. The pressure-pulse-wave sensor 36 is accommodated in the housing 30, and includes the press surface 34 in which a number of pressure-sensing elements, $E_{xy}$, are provided in a matrix, as shown in FIG. 3. The diaphragm 40 supports, in the housing 30, the pressure-pulse-wave sensor 36 such that the sensor 36 is movable in a direction to project out of the opening 28, and defines an airtight, pressure chamber 38 in the back of the sensor 36. The diaphragm 40 is formed of a thin elastic sheet.

More specifically described, as shown in FIG. 3, the pressure-pulse-wave sensor 36 has, in the press surface 34, the matrix of pressure-sensing elements Exy (x=1 to m, y=1 to n; m and n are natural numbers). The matrix of pressure-sensing elements Exy include a plurality of rows which extend along a plurality of reference lines, $L_{Y1}$ to $L_{Yn}$, respectively, which are parallel to each other and are arranged at a regular interval of distance, $d_y$, in a y direction which is made, when the sensor 36 is pressed against the carotid artery 22, generally parallel to a lengthwise direction of the carotid artery 22. Each of the rows consists of a plurality of pressure-sensing elements $E_{1y}$ to $E_{my}$ which are arranged at a regular interval of distance, $d_x$, in an x direction which is perpendicular to the y direction and which, when the sensor 36 is pressed against the carotid artery 22, traverses or intersects the artery 22. In the present embodiment, the regular interval $d_x$ is 0.6 mm, and each row is provided by fifteen or more pressure-sensing elements $E_{1y}$ to $E_{my}$ so that the each row extends, in the x direction, over a range greater than the diameter (or width) of the carotid artery 22, e.g., 8 mm.

Figure 6:
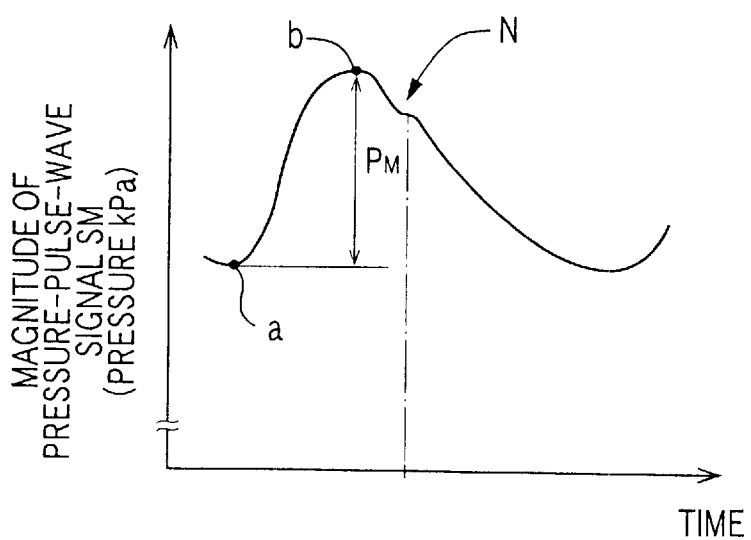
FIG. 6 is a view of the pressure-pulse-wave signal produced by each of the pressure-sensing elements of the matrix.

The press surface 34 of the pressure-pulse-wave sensor 36 is provided by, e.g., a semiconductor plate, and each of the pressure-sensing elements $E_{xy}$ is provided by a bridge including four strain gauges which are formed, by photolithography, in respective locally thinned portions of the semiconductor plate. Each pressure-sensing element $E_{xy}$ detects a strain produced in the corresponding, thinned portion, that is, detects a local pressure applied to the thinned portion, and produces a pressure signal representing the detected local pressure, i.e., a pressure-pulse-wave signal, SM, as shown in FIG. 6. Thus, the pressure-sensing elements Exy arranged in the matrix detect the respective local pressures applied to the press surface 34 of the pressure-pulse-wave sensor 36, and supply the respective pressure-pulse-wave signals SM representing the respective detected local pressures, to the control device 18 via a multiplexer 42 and an A/D converter 44.

The pressure chamber 38 defined in the housing 30 is connected to an air pump 46 via a pressure-control valve 48, and is supplied with a pressurized air which is initially produced by the air pump 46 and whose pressure is controlled by the pressure-control valve 48 in response to a control signal supplied thereto from the control device 18. Thus, the control device 18 can automatically change or adjust a pressing force with which the pressure-pulse-wave sensor 36 is pressed against the carotid artery 22 via the skin.

The control device 18 is provided by a so-called microcomputer including a central processing unit (CPU), a read only memory (ROM), a random access memory (RAM), and input and output interfaces. The CPU processes input signals according to control programs pre-stored in the ROM, by utilizing a temporary-storage function of the RAM. More specifically described, the CPU determines the bifurcate portion $22_D$ of the carotid artery 22; determines, as a pulse-wave-detect portion, SP, (FIG. 7) of the artery 22, a portion of the artery 22 that is distant by a predetermined distance downstream of the bifurcate portion $22_D$ in the direction of flow of blood in the artery 22; determines the second heart sound, as a first reference point, represented by the heart-sound signal SH detected by the heart-sound microphone 14; determines a second reference point on the pressure-pulse-wave signal SM produced by one of the pressure-sensing elements $E_{xy}$ positioned right above the pulse-wave-detect portion SP; calculates, as a pulse-wave propagation time, DT, a time difference between the first reference point determined on the heart-sound signal SH and the second reference point determined on the pressure-pulse-wave signal SM; calculates a pulse-wave propagation velocity, PWV (=L/DT; L is the distance between the heart and the pulse-wave-detect portion SP), based on the pulse-wave propagation time DT; calculates an estimated blood-pressure value, $E_{SYS}$, of the subject according to a predetermined relationship (i.e., $E_{SYS}=\alpha \cdot PWV+\beta$); and controls a display device 50 to display the thus obtained results.

Figure 4:
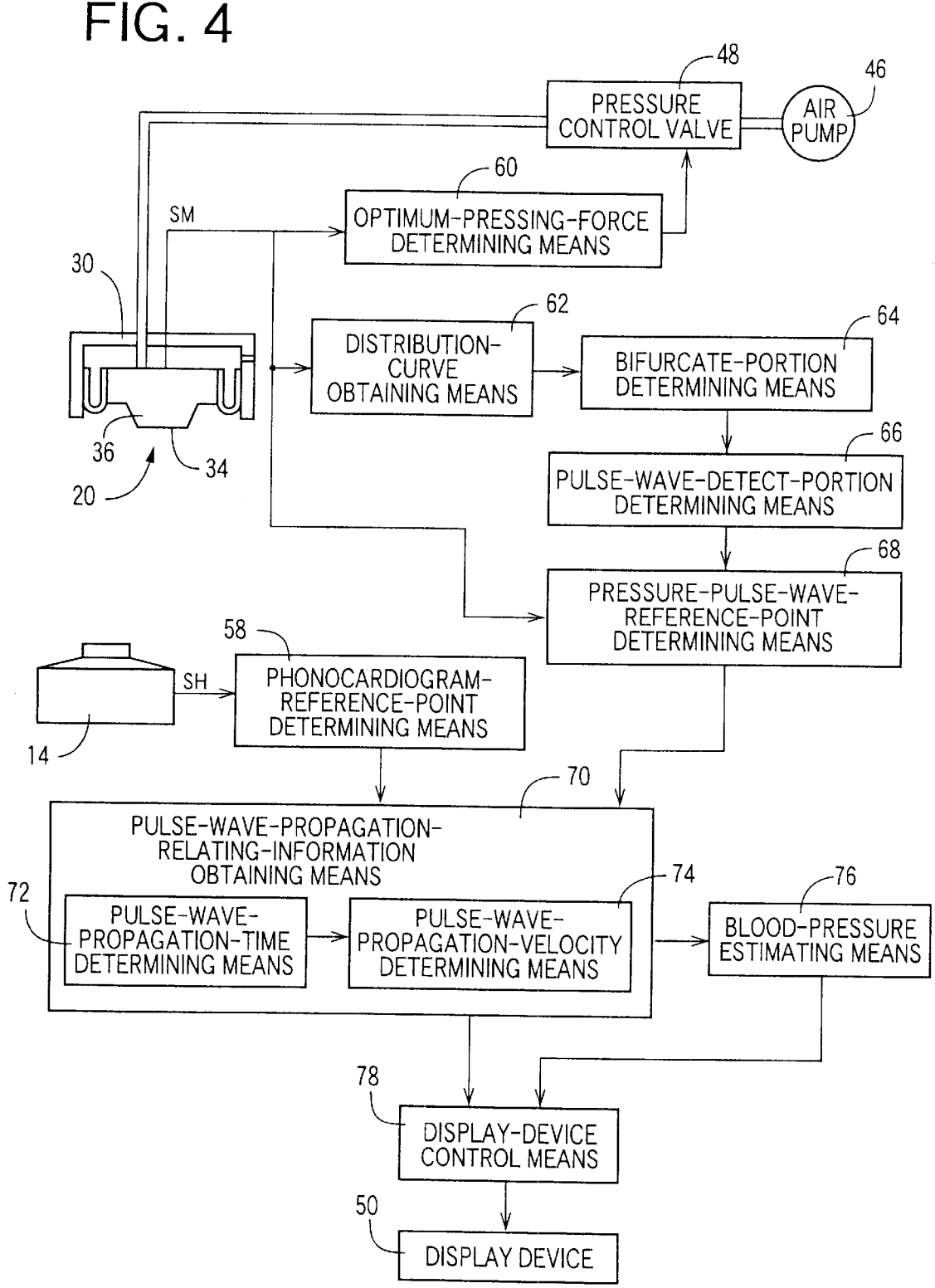
FIG. 4 is a diagrammatic view of relevant control functions of a control device of the apparatus of FIG. 1.

FIG. 4 is a diagrammatic view for explaining various functions of the control device 18 of the PWP-relating-information obtaining apparatus 12. A phonocardiogram-reference-point determining means 58 finds, on the heart-sound or phonocardiogram signal SH supplied from the heart-sound microphone 14, a time when a second heart sound, II, indicating the closure of the aortic valve occurs, and determines the thus found time as a phonocardiogram reference point as the first reference point.

Figure 5:
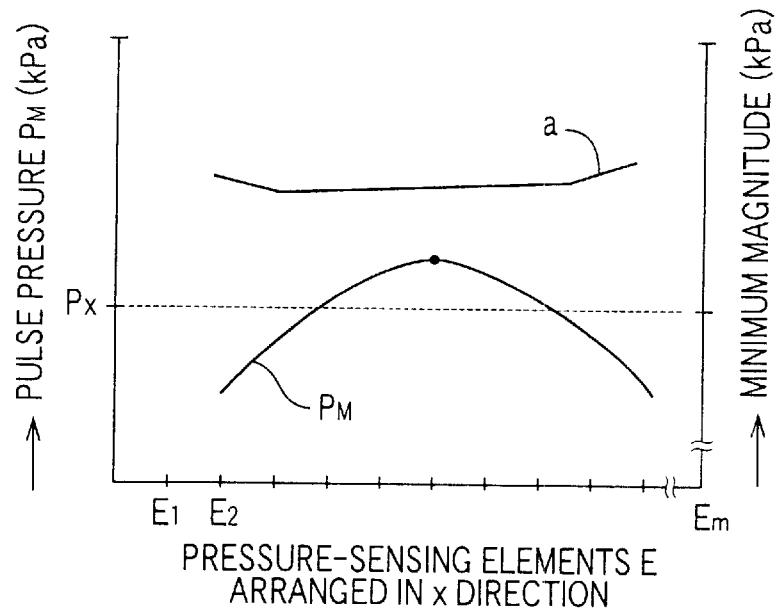
FIG. 5 is a view of a pulse-pressure tonogram as a distribution curve representing a relationship between respective positions of the pressure-sensing elements of one row of the matrix that traverse a carotid artery of the subject and respective pulse pressures represented by respective pressure-pulse-wave signals produced by the pressure-sensing elements.

An optimum-pressing-force determining means 60 controls the pressure-control valve 48 to change and maintain the air pressure in the chamber 38, to and at an optimum air pressure as an optimum pressing force, in such a manner that, as shown in a lower portion of the graph of FIG. 5, the middle (or nearly middle) one of the pressure-sensing elements E of the middle row, extending in the x direction, provides the greatest pulse pressure, $P_M$, of pressure-pulse-wave signal SM, in a distribution curve (i.e., a pulse-pressure tonogram) connecting the respective pulse pressures $P_M$ of pressure-pulse-wave signals SM produced by all the elements E of the middle row, and simultaneously the greatest pulse pressure $P_M$ is greater than a reference value, $P_X$, or alternatively, in such a manner that, as shown in an upper portion of the graph of FIG. 5, a middle portion of a distribution curve (i.e., a minimum-magnitude tonogram) connecting respective minimum magnitudes, a, of the pressure-pulse-wave signals SM produced by all the pressure-sensing elements E of the middle row, is substantially flat. Thus, the pressure-pulse-wave sensor 36 is pressed, with the optimum pressing force, against the carotid artery 22. A pulse pressure $P_M$ of pressure-pulse-wave signal SM is defined as an amplitude of a heartbeat-synchronous pulse of the signal SM, i.e., a pressure difference between the maximum magnitude, b, of the pulse and the minimum magnitude, a, of the pulse, as illustrated in the graph of FIG. 6. In the graph of FIG. 6, the magnitude, b, corresponds to an upper peak of the pulse, the magnitude, a, corresponds to the lower peak (i.e., the rising point) of the pulse, and a symbol, N, indicates a notch of the pulse.

Figure 7:
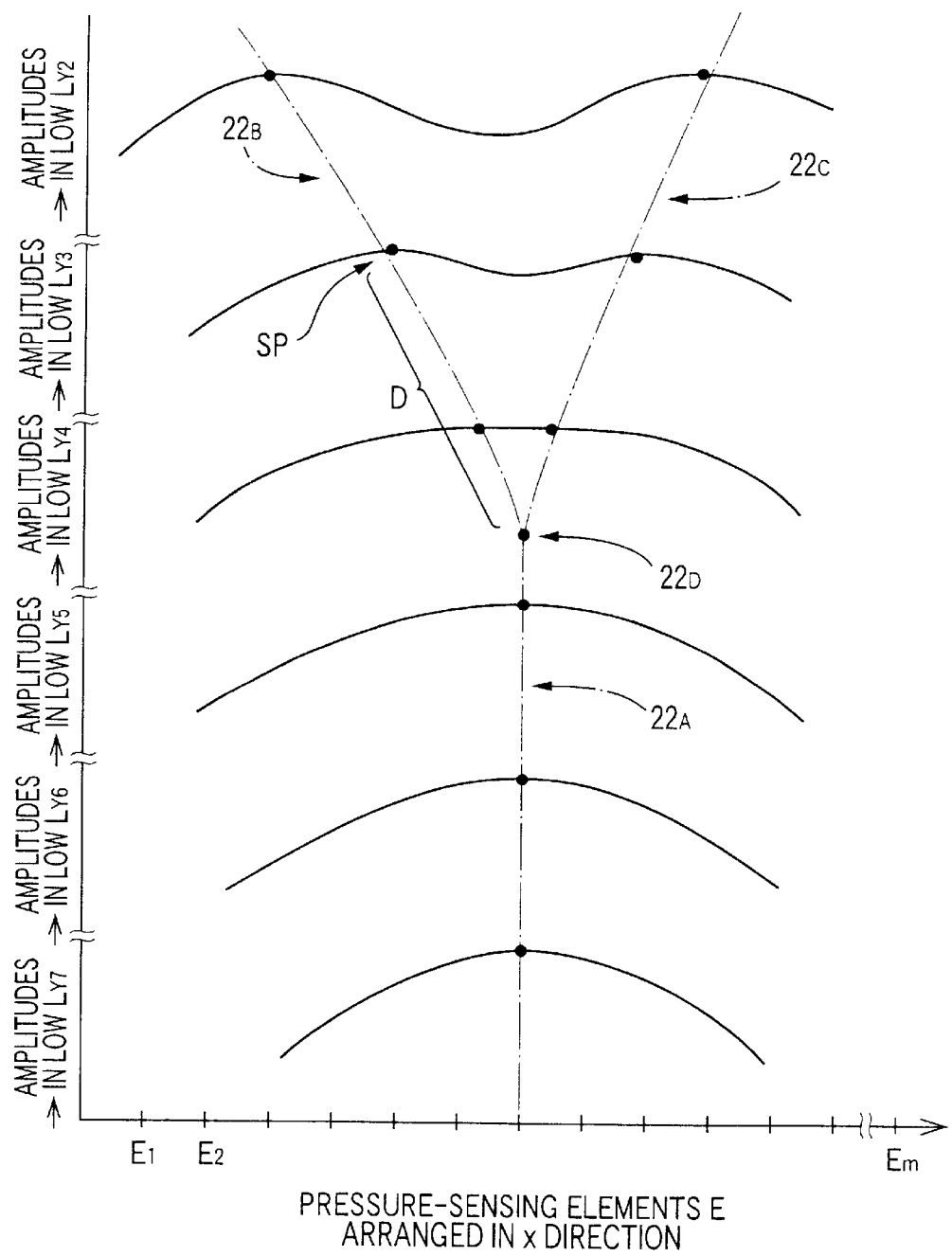
FIG. 7 is a view of the pulse-pressure tonograms which are obtained, by a distribution-curve obtaining means 62 shown in FIG. 4, from a predetermined range in a lengthwise direction of the carotid artery that includes a bifurcate portion of the carotid artery.

A distribution-curve obtaining means 62 obtains, from the respective pressure-pulse-wave signals SM produced by all the pressure-sensing elements $E_{xy}$ of the pressure-pulse-wave sensor 36 being pressed with the optimum pressing force, a plurality of distribution curves (i.e., a plurality of pulse-pressure tonograms), as shown in FIG. 7, corresponding to the plurality of rows extending along the plurality of reference lines $L_{Y1}$ to $L_{Yn}$, respectively. More specifically described, the distribution-curve obtaining means 62 first calculates respective pulse pressures $P_M$ of all the pressure-pulse-wave signals SM, and then calculates, by utilizing the technique of linear or curve interpolation, a distribution curve connecting the respective pulse pressures of the signals SM produced by the elements E of each of the rows which extend along the reference lines $L_{Y1}$ to $L_{Yn}$, respectively. In the state in which the pressure-pulse-wave sensor 36 is pressed against the carotid artery 22 via the skin, the plurality of rows of the matrix or the plurality of reference lines $L_{Y1}$ to $L_{Yn}$ correspond to a plurality of different portions of the artery 22 that are located within a predetermined range which extends in a lengthwise direction of the artery 22 and should include the bifurcate portion $22_D$ of the same 22.

A bifurcate-portion determining means 64 first selects, from the plurality of distribution curves shown in FIG. 7, one or more first curves (e.g., $L_{Y7}$, $L_{Y6}$, $L_{Y5}$) each of which has only one peak, and one or more second curves (e.g., $L_{Y3}$, $L_{Y2}$) each of which has two significant peaks, and then selects one or more intervals $d_y$ between the reference line $L_Y$ corresponding to one of the first curves that is the nearest to the second curves, and the reference line $L_Y$ corresponding to one of the second curves that is the nearest to the first curves. Regarding the example shown in FIG. 7, the bifurcate-portion determining means 64 selects the two intervals $d_y$ between the reference line $L_{Y5}$ and the reference line $L_{Y3}$, and specifies the bifurcate portion $22_D$ of the artery 22 based on the thus selected two intervals, specifically, within those two intervals. Described in more detail, the bifurcate-portion determining means 64 specifies respective peaks of all the pulse-pressure distribution curves shown in FIG. 7, and calculates, by the technique of linear or curve interpolation, two connection lines, each indicated at one-dot chain line, one of which connects the respective peaks of the above-indicated first curves and respective first peaks of the above-indicated second curves and the other of which connects the respective peaks of the first curves and respective second peaks of the second curves. If the thus obtained two connection lines are bifurcated or separated from each other, like capital letter, Y, within the above-indicated two intervals $d_y$, the bifurcate-portion determining means 64 determines, as the bifurcate portion $22_D$ of the carotid artery 22, a portion of the artery 22 that corresponds to the point or position where the two connection lines are bifurcated. A pressure-sensing element $E_{xy}$ more distant from the centerline of width of the radial artery 22 provides a pressure-pulse-wave signal SM with a smaller, attenuated pulse pressure $P_M$. Therefore, the peak of each pulse-pressure distribution curve corresponds to the centerline of the carotid artery 22. Thus, if the above-indicated two connection lines, indicated at one-dot chain lines in FIG. 7, are bifurcated like capital letter Y, the point of bifurcation of the connection lines corresponds to the bifurcate portion $22_D$ of the artery 22. A portion of the carotid artery 22 that is upstream of the bifurcate portion $22_D$ corresponds to the common carotid artery $22_A$, and respective portions of the carotid artery 22 that are downstream of the bifurcate portion $22_D$ correspond to the internal and external carotid arteries $22_B$, $22_C$. In the present embodiment, the carotid-pulse-wave detecting device 20 cooperate with respective portions of the control device 18 that correspond to the distribution-curve obtaining means 62 and the bifurcate-portion determining means 64, to provide an arterial-bifurcate-portion determining apparatus.

A pulse-wave-detect-portion determining means 66 determines, based on the thus determined bifurcate portion $22_D$ of the carotid artery 22, a pulse-wave-detect portion SP of the artery 22 from which a pressure pulse wave is detected to measure a pulse-wave propagation time DT. More specifically described, the determining means 66 determines, as the pulse-wave-detect portion SP, a portion of the internal carotid artery $22_B$ or the external carotid artery $22_C$ that is distant by a predetermined distance, D, downstream of the bifurcate portion $22_D$. The distance D is experimentally determined such that a pressure pulse wave detected from the pulse-wave-detect portion SP distant by the distance D from the bifurcate portion $22_D$ is substantially free of influences caused by turbulent flows which are likely to be produced around the bifurcate portion $22_D$. Regarding the example shown in FIG. 7, the determining means 66 determines, as the pulse-wave-detect portion SP, a portion of the internal carotid artery $22_B$.

A pressure-pulse-wave-reference-point determining means 68 first selects one of the pressure-sensing elements $E_{xy}$ of the matrix that is the nearest to the thus determined pulse-wave-detect portion SP of the carotid artery 22. Regarding the example shown in FIG. 7, the element $E_{73}$ is selected. Then, the determining means 68 finds or identifies, from the pressure-pulse-wave signal SM produced by the thus selected, nearest element E, a notch N (FIG. 6) indicating the closure of the aortic valve, as the reference point on the signal SM, and determines a time when the notch N occurs.

A PWP-relating-information obtaining means 70 includes a PWP-time determining means 72 for successively calculating, in synchronism with each of successive heartbeats of the subject, a time difference between the first reference point (i.e., the second heart sound II) on a corresponding heartbeat-synchronous pulse of the heart-sound signal SH and the second reference point (i.e., the notch N) on a corresponding heartbeat-synchronous pulse of the pressure-pulse-wave signal SM, and determines the thus calculated time difference as a pulse-wave propagation time DT for the each heartbeat. The obtaining means 70 additionally includes a PWP-velocity determining means 74 for successively determining, for the each heartbeat, a pulse-wave propagation velocity PWV (=L/DT) based on the thus determined propagation time DT and a predetermined propagation distance L between the heart and the pulse-wave-detect portion SP. The distance L is experimentally obtained in advance.

A blood-pressure estimating means 76 calculates, for the each heartbeat, an estimated blood-pressure value, $E_{SYS}$, based on the actually obtained propagation time DT or propagation velocity PWV, according to a predetermined relationship (i.e., $E_{SYS}=\alpha \cdot PWV+\beta$ or $E_{SYS}=\alpha \cdot L/DT+\beta$). A display-device control means 78 controls the display device 50 to display, in digital values or analogue values, or in the form of time-wise changing graphs, the pulse-wave propagation time DT determined by the means 72, the pulse-wave propagation velocity PWV determined by the means 74, and the estimated blood-pressure value ESYS calculated by the means 76.

Figure 8:
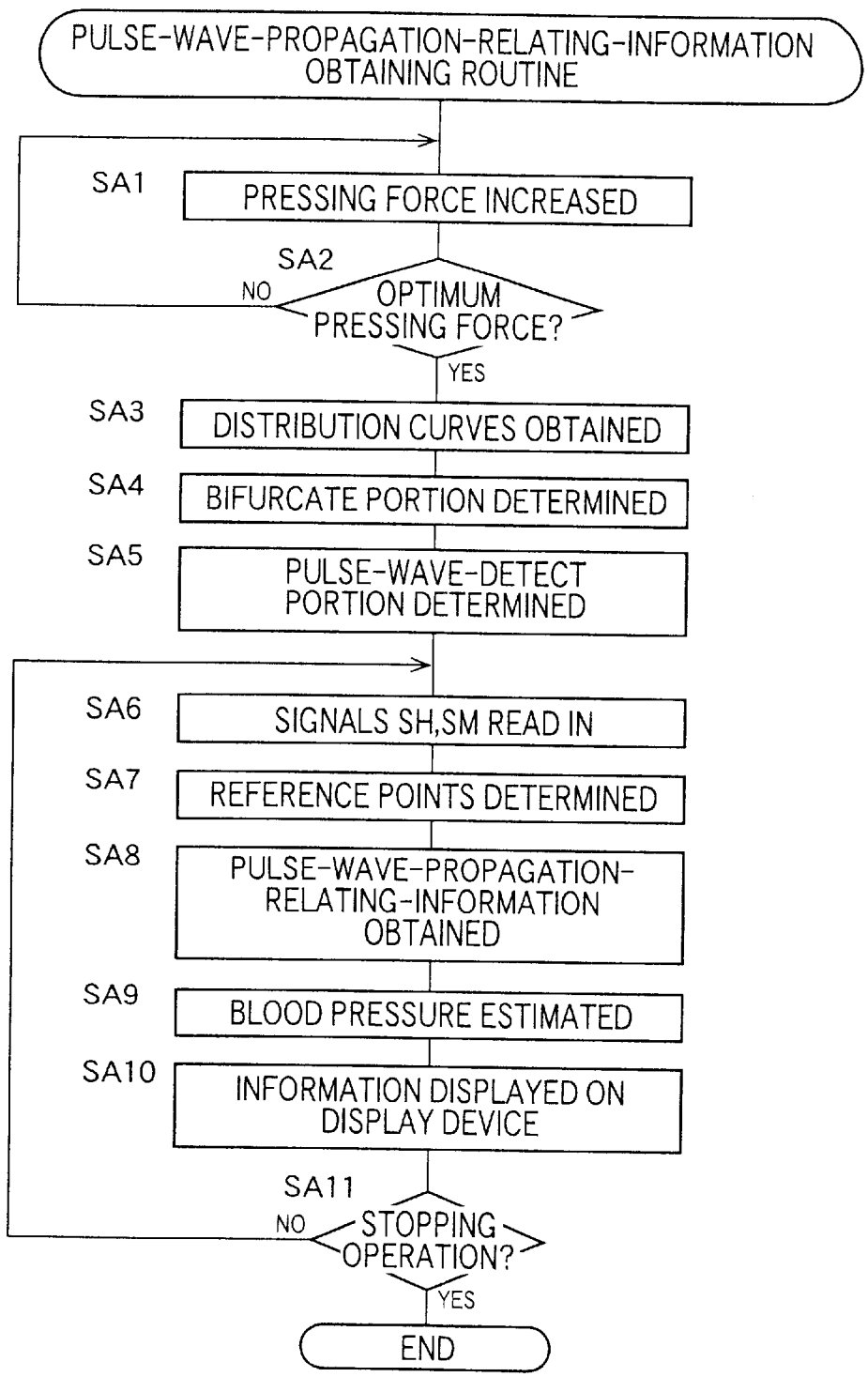
FIG. 8 is a flow chart representing a pulse-wave-propagation (PWP) relating information obtaining routine according to which the apparatus of FIG. 1 obtains PWP-relating information of the subject.

FIG. 8 is a flow chart representing a control program according to which the control device 18 controls the operation of the PWP-relating-information obtaining apparatus 12. This program is carried out in response to operation of a key (not shown) to start a PWP-relating-information obtaining operation. First, in Step SA1, the control device 18 operates the pressure control valve 48 to increase the air pressure in the pressure chamber 38 so that the pressing force with which the pressure-pulse-wave sensor 36 is pressed is increased from zero to a predetermined positive value. Next, in Step SA2, the control device 18 judges whether the pressing force applied to the sensor 36 has been increased to an optimum pressing force, based on the pulse-pressure tonogram, as shown in FIG. 5, obtained from the sensor 36. In an initial control cycle according to this routine, a negative judgment is made in Step SA2, and accordingly the control device 18 repeats Steps SA1 and SA2, so that the pressing force applied to the sensor 36 is gradually increased. When the pressing force applied to the sensor 36 has been increased to an optimum pressing force, a positive judgment is made in Step SA2, and accordingly the control device 18 goes to Step SA3 and the following steps. Steps SA1 and SA2 correspond to the optimum-pressing-force determining means 60.

In Step SA3 corresponding to the distribution-curve obtaining means 62, the control device 18 obtains, from the pressure-pulse-wave signals SM produced by the pressure-sensing elements $E_{xy}$ of the pressure-pulse-wave sensor 36, a plurality of distribution curves, as shown in FIG. 7, each of which connects respective pulse pressures (i.e., respective amplitudes) $P_M$ obtained from the elements $E_{x1}$ to $E_{xn}$ belonging to a corresponding one of the rows extending along the reference lines $L_{Y1}$ to $L_{Yn}$. Then, in Step SA4 corresponding to the bifurcate-portion determining means 64, the control device 18 determines, by using the technique of linear or curve interpolation, two connection lines, as indicated at one-dot chain lines in FIG. 7, one of which connects respective peaks of one or more first distribution curves each having one peak (i.e., one maximum) and respective first peaks of one or more second distribution curves each having two peaks (i.e., two maxima) and the other of which connects the respective peaks of the one or more first distribution curves and respective second peaks of the one or more second distribution curves. If the thus obtained two connection lines are bifurcated like capital letter Y within one or more intervals $d_y$ between one reference line $L_y$ corresponding to one of the first distribution curves that is the nearest to the second distribution curves, and another reference line $L_y$ corresponding to one of the second distribution curves that is the nearest to the first distribution curves, the control device 18 determines, as the bifurcate portion $22_D$ of the carotid artery 22, a portion of the artery 22 that corresponding to the point or position where the two connection lines are bifurcated. However, the control device 18 may be modified such that if the two connection lines are bifurcated within the first and last reference lines $L_{Y1}$, $L_{Yn}$, it determines the bifurcate portion $22_D$ in the above-described manner.

In Step SA5 corresponding to the pulse-wave-detect-portion determining means 66, the control device 18 determines, as the pulse-wave-detect portion or position SP of the carotid artery 22, a portion of the internal or external carotid artery $22_B$, $22_C$ that is distant by the predetermined distance D downstream of the bifurcate portion $22_D$.

Next, in Step SA6, the control device 18 reads in a heartbeat-synchronous pulse of the phonocardiogram (i.e., heart-sound) signal SH and a corresponding heartbeat-synchronous pulse of the pressure-pulse-wave signal SM. The signal SH is supplied from the heart-sound microphone 14, and the signal SM is supplied from one (e.g., element $E_{73}$) of the pressure-sensing elements $E_{xy}$ that is the nearest to the pulse-wave-detect portion or position SP of the carotid artery 22. The respective pulses of the signal SH and the signal SM corresponds to each one heartbeat of the subject. Then, in Step SA7 corresponding to the phonocardiogram-reference-point determining means 58 and the pressure-pulse-wave-reference-point determining means 68, the control device 18 determines, as the reference point on the phonocardiogram signal SH produced by the heart-sound microphone 14, a time of occurrence of the second heart sound II indicating the closure of the aortic valve, and determines, as the reference point on the pressure-pulse-wave signal SM produced by the pressure-sensing element $E_{73}$, a time of occurrence of the notch N also indicating the closure of the aortic valve.

Next, in Step SA8 corresponding to the PWP-relating-information obtaining means 70, the control device 18 calculates, for the above-indicated one heartbeat of the subject, a time difference between the reference point on the phonocardiogram signal SH and the reference point on the pressure-pulse-wave signal SM, and determines the thus calculated time difference as the PWP time DT. In addition, the control device 18 determines, for the one heartbeat of the subject, a PWP velocity PWV (=L/DT) based on the thus determined PWP time DT and the predetermined propagation distance L between the heart and the pulse-wave-detect portion or position SP. Then, in Step SA9 corresponding to the BP estimating means 76, the control device 18 determines, for the one heartbeat of the subject, an estimated BP value $E_{SYS}$ based on the PWP time DT or the PWP velocity PWV according to the predetermined relationship between estimated BP values and PWB-relating information (i.e., $E_{SYS}=\alpha \cdot L/DT+\beta$ or $E_{SYS}=\alpha \cdot PWV+\beta$). Then, in Step SA10 corresponding to the display-device control means 78, the control device 18 operates the display device 50 (e.g., a cathode ray tube or a printer) to display, in digital or analogue values, the PWP time DT and the PWP velocity PWV determined in Step SA8 in the current control cycle and the estimated BP value $E_{SYS}$ determined in Step SA9 in the current control cycle, and additionally display three trend graphs representing respective time-wise changes of the three parameters DT, PWV, $E_{SYS}$ measured in successive control cycles according to this routine.

In Step SA11, the control device 18 judges whether a key (not shown) has been operated to stop the current PWP-relating-information obtaining operation. So long as a negative judgment is made in Step SA11 in each of successive control cycles, the control device 18 repetitively carries out Steps SA6 and the following steps to read in each of successive heartbeat-synchronous pulses of the phonocardiogram signal SH and a corresponding one of successive heartbeat-synchronous pulses of the pressure-pulse-wave signal SM, and determine, for each of successive heartbeats of the subject, a piece of PWP-relating information (i.e., a PWP time DT and a PWP velocity PWV) and an estimated BP value. Meanwhile, if a positive judgment is made at Step SA11, the control device 18 quits the present routine after removing the pressing force applied to the pressure-pulse-wave sensor 36 in an additional step (not shown).

It emerges from the foregoing description that in the present embodiment, the pulse-wave-detect-portion determining means 66 (Step SA5) determines the pulse-wave-detect portion or position SP of the carotid artery 22 based on the bifurcate portion $22_D$ of the artery 22 determined by the bifurcate-portion determining means 64 (Step SA4) as part of the bifurcate-portion determining apparatus, then the pressure-pulse-wave-reference-point determining means 68 (Step SA7) determines the reference point on the pressure pulse wave detected from the pulse-wave-detect portion or position SP, and the PWP-relating-information obtaining means 70 (Step SA8) obtains the PWP-relating information based on the reference point on the pressure pulse wave. Since the pulse-wave-detect portion or position SP is determined based on the bifurcate portion $22_D$ of the carotid artery 22 itself, and the PWP-relating information is obtained based on the reference point on the pressure pulse wave detected from the pulse-wave-detect portion SP, substantially the same portion of the artery 22 can be determined, without being influenced by changes of posture of the subject, as the pulse-wave-detect portion SP in each of a plurality of PWP-relating-information obtaining operations each according to the routine shown in FIG. 8, and a plurality of pieces of accurate PWP-relating information can be obtained. This advantage is particularly important because the PWP-relating information is obtained based on the small time difference between the reference point on the waveform of phonocardiogram and the reference point on the waveform of pressure pulse wave detected from the carotid artery 22. The small time difference means the small propagation distance over which the pressure pulse wave propagates from the heart to the pulse-wave-detect portion or position SP of the artery 22.

In addition, in the present embodiment, the above-indicated bifurcate-portion determining apparatus includes the distribution-curve obtaining means 62 (Step SA3) which obtains the plurality of distribution curves each of which represents the relationship between the respective positions of at least one row of pressure-sensing elements $E_{xy}$ arranged at the regular interval $d_x$ of distance in the x direction and the respective amplitudes (i.e., pulse pressures $P_M$) of the respective pressure-pulse-wave signals SM produced by the array of elements $E_{xy}$ which is located at a corresponding one of the plurality of positions (i.e., a corresponding one of the reference lines $L_{Yn}$) which are arranged at the regular interval $d_y$ of distance in the predetermined range $L_{Y1}$ to $L_{Yn}$ in the lengthwise direction of the artery 22 and at each of which the array of elements $E_{xy}$ extending in the x direction traverses the artery 22; and the bifurcate-portion determining means 64 (Step SA4) which determines, based on the distribution curves respectively corresponding to the positions $L_{Yn}$, the bifurcate portion $22_D$ of the artery 22 in the predetermined range in the lengthwise direction of the artery 22. Therefore, the bifurcate portion $22_D$ of the carotid artery 22 can be accurately determined, and accordingly accurate PWP-relating information can be obtained.

In addition, in the present embodiment, the bifurcate-portion determining means 64 (Step SA4) selects the bifurcate portion $22_D$ of the carotid artery 22 based on the one or more intervals $d_y$ where one or more pulse-pressure distribution curves each having one peak change to one or more distribution curves each having two peaks, specifically within the range corresponding to the selected intervals. Thus, the bifurcate portion $22_D$ of the artery 22 can be accurately determined, and accurate PWP-relating information can be obtained.

Moreover, in the present embodiment, the pulse-wave-detect-portion determining means 66 (Step SA5) determines, as the pulse-wave-detect portion or position SP, a portion of the carotid artery 22 that is distant by the predetermined distance downstream of the bifurcate portion $22_D$ of the artery 22. Therefore, the pressure pulse wave detected from the pulse-wave-detect portion SP of the carotid artery 22 is free of influences of turbulent flows which are likely to occur around the bifurcate portion $22_D$ of the artery 22. Thus, the reference point can be accurately determined on the waveform of pressure pulse wave. In addition, since the distance of propagation of the pressure pulse wave is extended from the bifurcate portion $22_D$ to the pulse-wave-detect portion SP, the PWP time DT and the PWP velocity PWV can be accurately determined.

In addition, in the present embodiment, the PWP-relating-information obtaining means 70 (Step SA) obtains the PWP-relating information based on the time difference DT between the reference point determined on the waveform of phonocardiogram and the reference point determined on the waveform of pressure pulse wave detected from the pulse-wave-detect portion SP of the carotid artery 22. The thus obtained waveform of pressure pulse wave is substantially identical with that of pressure pulse wave detected directly from the aorta of the subject, and the reference point is determined on this waveform. Accordingly, although the carotid artery 22 is considerably near to the heart of the subject, accurate PWP-relating information can be obtained.

Moreover, in the present embodiment, the pressure-pulse-wave sensor 36 includes the plurality of pressure-sensing elements $E_{xy}$ which are provided, in the press surface 34, in a matrix, that is, are arranged at the regular interval of distance $d_x$ along the plurality of first straight lines $L_{Yn}$ parallel to each other and at the regular interval of distance $d_y$ along a plurality of second straight lines which are parallel to each other and are perpendicular to the first straight lines $L_{Yn}$. Therefore, in the present embodiment, a drive device is not needed, which can move the sensor 36 in directions along the carotid artery 22, in contrast to the case where the sensor 36 is provided by a single array of pressure-sensing elements which traverses or intersects the artery 22 in a state in which the sensor 36 is pressed against the artery 22 via the skin.

While the present invention has been described in its preferred embodiment, the invention may otherwise be embodied.

For example, though the illustrated bifurcate-portion determining apparatus as part of the illustrated PWP-relating-information obtaining apparatus 12 determines the bifurcate portion $22_D$ of the carotid artery 22, the means 64 may be adapted to determine a bifurcate portion of a different artery such as a dorsal pedal artery.

In addition, while in the illustrated PWP-relating-information obtaining apparatus 12 the bifurcate-portion determining means 64 determines the bifurcate portion $22_D$ of the carotid artery 22 based on the pulse-pressure distribution curves obtained by pressing the pressure-pulse-wave sensor 36 against the artery 22 via the skin, the means 64 may be modified to determine, by ultrasonography or MRI method, the bifurcate portion $22_D$ of the artery 22, without needing contact with the skin of the subject.

Although in the illustrated embodiment the carotid-artery-pulse-wave detecting device 20 employs the pressure-pulse-wave sensor 36 which has the matrix of pressure-sensing elements $E_{xy}$ in the press surface 34, the detecting device 20 may employ a different pressure-pulse-wave sensor which has an array of pressure-sensing elements $E_x$ which are arranged at a regular interval of distance along a straight line which traverses or intersects the carotid artery 22 when the sensor is pressed against the artery 22 via the skin. In the latter case, the sensor is moved, by being driven by an electric motor, or manually, within a predetermined range which extends in the lengthwise direction of the artery 22 and should encompass the bifurcate portion $22_D$ of the artery 22.

In addition, in the illustrated embodiment, the carotid-artery-pulse-wave detecting device 20 includes the pressure chamber 38, the elastic diaphragm 40, the pressure control valve 48, and the air pump 46 which cooperate with one another to press the pressure-pulse-wave sensor 36 against the carotid artery 22. However, those elements 38, 40, 48, 46 may be replaced with a spring as a biasing device. In the latter case, the optimum-pressing-force determining means 60 is not provided.

In the illustrated embodiment, the PWP-relating-information obtaining means 70 obtains the PWP-relating information based on the time difference DT between the reference point on the phonocardiogram signal SH and the reference point on the pressure-pulse-wave signal SM obtained from the pulse-wave-detect portion SP of the carotid artery 22.

However, the phonocardiogram signal SH produced by the heart-sound microphone 14 may be replaced with an electrocardiogram (ECG) signal produced by an ECG device, and an R wave may be determined as a reference point on the waveform of ECG signal. In addition, the notch N (FIG. 6) as the reference point on the waveform of pressure-pulse-wave signal SM may be replaced with a rising point (i.e., a minimum-magnitude point or a lower-peak point), a maximum-slope point, or a maximum-magnitude point on the waveform of signal SM. Moreover, a time difference DT may be measured between a reference point on the waveform of signal SM obtained from the pulse-wave-detect portion SP of the carotid artery 22 and a subsequently detected reference point on the waveform of, e.g., a pressure pulse wave which is detected by a pressure-pulse-wave sensor pressed against a radial artery, a volumetric pulse wave which is obtained from a cuff wound around an upper arm or a leg, or a photoelectric pulse wave which is detected by a photoelectric-pulse-wave sensor worn on a finger or an earlobe.

In the illustrated embodiment, the pulse-wave-detect-portion determining means 66 determines, as the pulse-wave-detect portion SP of the carotid artery 22, a portion or position of the artery 22 that is distant by the predetermined distance D downstream of the bifurcated portion $22_D$ in the direction of flow of blood in the artery 22. However, the means 66 may be modified to determine, as the pulse-wave-detect portion SP, a portion of the artery 22 that is distant by a predetermined distance upstream of the bifurcated portion $22_D$ in the direction of flow of blood in the artery 22. In a particular case where a strong pressure-pulse-wave signal SM is needed, the bifurcate portion $22_D$ itself may be determined as the pulse-wave-detect portion SP, because the signal SM detected from the bifurcate portion $22_D$ is considerably strong.

In the illustrated embodiment, Steps SA6 and the following steps are successively or consecutively carried out in synchronism with each of successive heartbeats of the subject, so that the PWP-relating-information obtaining means 70 obtains a piece of PWP-relating information for the each heartbeat of the subject. However, Steps SA6 and the following steps may be modified to obtain a piece of PWP-relating information for every second, third, . . . , or n-th heartbeat of the subject, or at a predetermined period.

In the illustrated embodiment, the distribution-curve obtaining means 62 obtains, from the pressure-pulse-wave signals SM produced by the pressure-sensing elements $E_{xy}$ of the pressure-pulse-wave sensor 36 being pressed against the carotid artery 22 via the skin, the pulse-pressure tonograms, i.e., the distribution curves each of which connects the respective pulse pressures $P_M$ of the respective pressure pulse waves obtained from a corresponding one of the rows respectively extending along the reference lines $L_{Y1}$ to $L_{Yn}$ each of which traverses the artery 22 in the state in which the sensor 36 is pressed against the artery 22. However, the pulse-pressure tonograms may be replaced with minimum-magnitude tonograms, i.e., distribution curves each of which connects the respective minimum magnitudes (a, shown in FIG. 5) of the respective pressure pulse waves obtained from a corresponding one of the rows respectively extending along the reference lines $L_{Y1}$ to $L_{Yn}$.

It is to be understood that the present invention may be embodied with other changes, modifications and improvements which may occur to a person skilled in the art, without departing from the spirit and scope of the invention defined in the appended claims.

What is claimed is:

1. An apparatus for obtaining a pulse-wave-propagation-relating information of a living subject, comprising:
   a bifurcate-portion determining device which determines a bifurcate portion of an artery of the subject that is present under a skin of the subject;
   a pulse-wave-detect-portion determining means for determining, based on the determined bifurcate portion of the artery, a pulse-wave-detect portion of the artery from which a pulse wave is detected;
   a reference-point determining means for determining a reference point on the pulse wave detected from the determined pulse-wave-detect portion of the artery; and
   a pulse-wave-propagation-relating-information obtaining means for obtaining the pulse-wave-propagation-relating information of the subject based on the determined reference point of the pulse wave.

2. An apparatus according to claim 1, wherein the bifurcate-portion determining device comprises:
   a pressure-pulse-wave sensor including a plurality of pressure-sensing elements which are arranged at a first regular interval of distance in an arrangement direction over a distance longer than a diameter of the artery, and each of which produces a pulse-wave signal representing a pressure pulse wave propagated thereto from the artery;

a distribution-curve obtaining means for obtaining a plurality of distribution curves each of which represents a relationship between respective positions of the pressure-sensing elements in the arrangement direction and respective amplitudes or respective minimum magnitudes of the respective pressure pulse waves represented by the respective pulse-wave signals produced by the pressure-sensing elements which are located at a corresponding one of a plurality of curve-obtain positions which are arranged at a second regular interval of distance in a predetermined range in a lengthwise direction of the artery and at each of which the pressure-sensing elements arranged in the arrangement direction traverse the artery; and a bifurcate-portion determining means for determining, based on the distribution curves respectively corresponding to the curve-obtain positions, the bifurcate portion of the artery in the predetermined range in the lengthwise direction of the artery.

3. An apparatus according to claim 2 wherein the pulse-wave-detect-portion determining means determines, as the pulse-wave-detect portion of the artery, a portion of the artery that is distant, by a predetermined distance, downstream of the determined bifurcate portion of the artery in a direction in which blood flows in the artery.

4. An apparatus according to claim 2 wherein the pulse-wave-propagation-relating-information obtaining means obtains the pulse-wave-progagation-relating information of the subject based on a time difference between a reference point on a waveform of an electrocardiogram or a phonocardiogram and the determined reference point of a pressure pulse wave as the pulse wave detected from the determined pulse-wave-detect portion of a carotid artery as the artery.

5. An apparatus according claim 2 wherein the bifurcate-portion determining means determines the bifurcate portion of the artery based on at least one second interval between the two curve-obtain positions one of which corresponds to the distribution curve having a single peak and the other of which corresponds to the distribution curve having two peaks.

6. An apparatus according to claim 5 wherein the pulse-wave-detect-portion determining means determines, as the pulse-wave-detect portion of the artery, a portion of the artery that is distant, by a predetermined distance, downstream of the determined bifurcate portion of the artery in a direction in which blood flows in the artery.

7. An apparatus according to claim 5 wherein the pulse-wave-propagation-relating-information obtaining means obtains the pulse-wave-propagation-relating information of the subject based on a time difference between a reference point on a waveform of an electrocardiogram or a phonocardiogram and the determined reference point of a pressure pulse wave as the pulse wave detected from the determined pulse-wave-detect portion of a carotid artery as the artery.

8. An apparatus according to claim 1, wherein the pulse-wave-detect-portion determining means determines, as the pulse-wave-detect portion of the artery, a portion of the artery that is distant, by a predetermined distance, downstream of the determined bifurcate portion of the artery in a direction in which blood flows in the artery.

9. An apparatus according to claim 8 wherein the pulse-wave-propagation-relating-information obtaining means obtains the pulse-wave-propagation-relating information of the subject based on a time difference between a reference point on a waveform of an electrocardiogram or a phonocardiogram and the determined reference point of a pressure pulse wave as the pulse wave detected from the determined pulse-wave-detect portion of a carotid artery as the artery.

10. An apparatus according to claim 1, wherein the pulse-wave-propagation-relating-information obtaining means obtains the pulse-wave-propagation-relating information of the subject based on a time difference between a reference point on a waveform of an electrocardiogram or a phonocardiogram and the determined reference point of a pressure pulse wave as the pulse wave detected from the determined pulse-wave-detect portion of a carotid artery as the artery.

11. An apparatus according to claim 2, wherein the pressure-pulse-wave sensor includes the pressure-sensing elements which are arranged in a matrix such that the elements are arranged at a regular interval of distance along a plurality of first straight lines parallel to each other and at a regular interval of distance along a pulrality of second straight lines which are parallel to each other and are perpendicular to the first straight lines.

12. An apparatus for determining a bifurcate portion of an artery of a living subject that is present under a skin of the subject comprising:

a pressure-pulse-wave sensor including a plurality of pressure-sensing elements which are arranged at a first regular interval of distance in an arrangement direction over a distance longer than a diameter of the artery, and each of which produces a pulse-wave signal representing a pressure pulse wave propagated thereto from the artery;

a distribution-curve obtaining means for obtaining a plurality of distribution curves each of which represents a relationship between respective positions of the pressure-sensing elements in the arrangement direction and respective amplitudes or respective minimum magnitudes of the respective pressure pulse waves represented by the respective pulse-wave signals produced by the pressure-sensing elements which are located at a corresponding one of a plurality of curve-obtain positions which are arranged at a second regular interval of distance in a predetermined range in a lengthwise direction of the artery and at each of which the pressure-sensing elements arranged in the arrangement direction traverse the artery; and a bifurcate-portion determining means for determring, based on the distribution curves respectively corresponding to the curve-obtain positions, the bifurcate portion of the artery in the predetermined range in the lengthwise direction of the artery.

13. An apparatus according to claim 12, wherein the bifurcate-portion determining means determines the bifurcate portion of the artery based on at least one second interval between the two curve-obtain positions one of which corresponds to the distribution curve having a single peak and the other of which corresponds to the distribution curve having two peaks.

* * * * *